United States Patent
Fillinger et al.

(10) Patent No.: US 11,727,326 B1
(45) Date of Patent: Aug. 15, 2023

(54) SYSTEMS AND METHODS FOR MANAGING TASKS USING THE INTERNET OF THINGS

(71) Applicant: United Services Automobile Association (USAA), San Antonio, TX (US)

(72) Inventors: Ryan James Fillinger, Prosper, TX (US); Richard Tanner, McKinney, TX (US); Joey Kessler, Melissa, TX (US); Layne Wiesendanger, Frisco, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 21 days.

(21) Appl. No.: 17/478,876

(22) Filed: Sep. 17, 2021

Related U.S. Application Data

(63) Continuation of application No. 15/427,910, filed on Feb. 8, 2017, now Pat. No. 11,151,888.

(60) Provisional application No. 62/292,942, filed on Feb. 9, 2016.

(51) Int. Cl.
*G06Q 10/0631* (2023.01)
*G06Q 40/00* (2023.01)
*G06Q 20/36* (2012.01)

(52) U.S. Cl.
CPC ....... *G06Q 10/06311* (2013.01); *G06Q 20/36* (2013.01); *G06Q 40/00* (2013.01)

(58) Field of Classification Search
None
See application file for complete search history.

(56) References Cited

U.S. PATENT DOCUMENTS

| | | |
|---|---|---|
| 2010/0136944 A1 | 6/2010 | Taylor et al. |
| 2011/0231218 A1 | 9/2011 | Tovar |
| 2011/0276896 A1 | 11/2011 | Zambetti et al. |
| 2012/0289254 A1 | 11/2012 | Dishneau |
| 2013/0013347 A1 | 1/2013 | Ling et al. |
| 2013/0115927 A1 | 5/2013 | Gruber et al. |
| 2014/0067691 A1 | 3/2014 | Pitroda et al. |
| 2014/0107894 A1 | 4/2014 | Obradovich |
| 2014/0247158 A1 | 9/2014 | Tengler et al. |
| 2014/0279420 A1 | 9/2014 | Okerlund et al. |
| 2014/0297348 A1 | 10/2014 | Ellis |
| 2015/0006296 A1 | 1/2015 | Gupta et al. |
| 2015/0095268 A1 | 4/2015 | Greenzeiger et al. |
| 2015/0120349 A1 | 4/2015 | Weiss |
| 2016/0087933 A1 | 3/2016 | Johnson et al. |
| 2016/0350060 A1 | 5/2016 | Park et al. |
| 2017/0053460 A1 | 2/2017 | Hauser et al. |
| 2017/0305349 A1 | 10/2017 | Naboulsi |
| 2018/0324562 A1 | 11/2018 | Park et al. |
| 2020/0202307 A1 | 6/2020 | Bos |

*Primary Examiner* — Nathan Hillery
(74) *Attorney, Agent, or Firm* — Perkins Coie LLP

(57) ABSTRACT

Methods and systems described in this disclosure are directed at delivery of educational concepts for increasing the financial literacy of youths. In some embodiments, a mobile application program is disclosed that facilitates management of tasks assigned to youths, setting up a rewards program for participants that complete tasks successfully on time, integrating different types of data from various devices to determine whether an assigned task is successfully completed. In some embodiments, the disclosed platform can integrate with electronic payment systems managed by external third parties for rewarding youths on successfully completing the task.

20 Claims, 11 Drawing Sheets

SYSTEMS AND METHODS FOR MANAGING TASKS USING THE INTERNET OF THINGS

CROSS-REFERENCE TO RELATED APPLICATIONS

This application is a continuation of U.S. patent application Ser. No. 15/427,910, filed Feb. 8, 2017, now allowed, which is a non-provisional of and claims priority to U.S. Provisional Application No. 62/292,942, filed on Feb. 9, 2016, entitled "SYSTEMS AND METHODS FOR MANAGING TASKS USING THE INTERNET OF THINGS," which is hereby incorporated by reference in its entirety for all purposes.

TECHNICAL FIELD

Various embodiments of the present disclosure generally relate to task management. More specifically, various embodiments of the present disclosure relate to methods and systems for automated task management based on data collected from a variety of electronic devices.

BRIEF DESCRIPTION OF THE DRAWINGS

Embodiments of the present disclosure will be described and explained through the use of the accompanying drawings in which.

DETAILED DESCRIPTION

Figure 1:
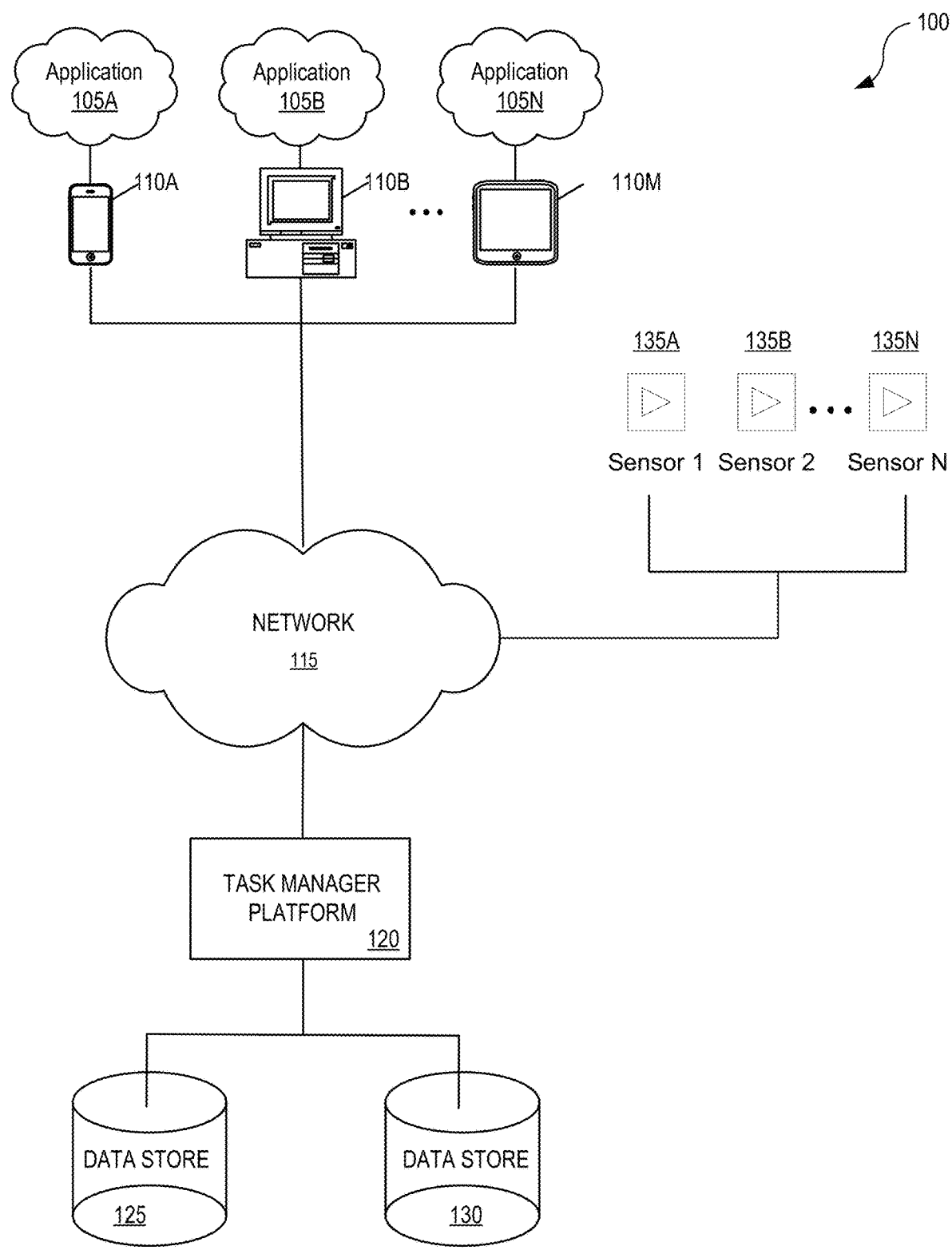
FIG. 1 illustrates an example of a network-based operating environment in accordance with various embodiments of the present disclosure.

Various embodiments of the present disclosure generally relate to task management. More specifically, various embodiments of the present disclosure relate to methods and systems for automated task management based on data collected from a variety of electronic devices. A party performing an assigned task can be provided a reward when the task is detected as completed. Such automated task management can be used in any number of applications, such as to increase financial literacy of youths. For example, using embodiments disclosed herein, when a task is detected by the electronic device as completed, youths can be rewarded with money, and, in doing so, can learn how to save money, create financial goals, and generate responsible spending habits. For example, when a task is completed, the child earns a reward. The reward may be money. The child can save money toward a goal (e.g., a new video game). In some embodiments, the child may be required to put at least a portion of any reward into a savings account. Thus, using systems and methods disclosed herein, children can be taught financial basics. Throughout the specification, the task assigner and the task assignee are referred to as the parent and the child (or youth), respectively, as examples only. It should be clear to one of ordinary skill in the art that the task assigner and the task assignee can be any type of relationship in which one party completes task for another party (e.g., supervisor/employee, insurance company/insured).

Methods and systems disclosed herein allow parents, child care providers, and/or legal guardians to create tasks for children via a mobile application program. In some embodiments, the child can create tasks for him or herself. The mobile application program can be used to manage tasks delegated or assigned to children by a task assigner such as a parent, child care provider, or a legal guardian or chosen by the child. In some embodiments, tasks may be automatically created based on sensor input or previous patterns of tasks. The disclosed system can inform both youths and parents of due dates for completion of the tasks and associated rewards.

In some embodiments, a child can also have access to a mobile application program or other device program (e.g., website). In such embodiments, the same mobile application program can be used by both a parent and a youth in operation, depending on who has logged into the mobile application program. For example, a parent can create a task to unload the dishwasher via the mobile application program. In turn, the child can be informed of the details of the task through a mobile application program running on the child's device. The parent can also set a time of completion of the task, as well as other goals or parameters associated with the task.

In some embodiments, a parent can provide instructions with the help of images, text, or videos in connection with completing the task. For example, if a parent has tasked a child with changing the oil in the car, the parent can send a demonstration video that teaches how to the change the oil. In some embodiments, the task can involve electronic devices, household appliances, or automobiles. For example, the electronic device can be a dishwasher, an oven, an automobile, a grill, a washer, a dryer, or a refrigerator. Examples of various tasks can, without limitation, be unloading a dishwasher, loading the dishwasher, rotating tires of an automobile, changing engine oil of an automobile, cleaning an oven, cleaning a grill, cleaning a refrigerator, going to a location in the automobile, or doing laundry. In some embodiments, the task can be a driving-related task that may involve a youth assigned to operate an automobile (e.g., a youth driving the parent's car to take a younger sibling to soccer practice. In some embodiments, the task can be a task that relates to healthy choices of the youth (e.g., running a few miles, or swimming for a certain time). Thus, any type of task is contemplated by the disclosure presented herein.

In some embodiments, tasks involving electronic devices or automobiles can communicate with the mobile application running on the parent's mobile device, for example, to detect various settings and parameters in the electronic device or automobile associated with the task. For example, a sensor in a dishwasher can inform the parent that the dishwasher needs to be unloaded or that the dishwasher has already been unloaded. In another example, the car can communicate telematics data to the parent's mobile device, enabling the parent to determine the driving abilities of the youth and whether or not the youth is adhering to various settings and parameters for the task in question. Examples of parameters can be driving below a certain speed limit, driving along a particular route, driving with the sound in the car stereo below a certain threshold volume level, driving with headlights on, driving without jackrabbit starts and stops, driving with seatbelts on, driving with a safe bumper distance from the automobile in front and rear, driving without too frequent lane changes, driving with roadside safety precautions, driving with the wipers on when it is raining, and following safe parking measures.

In some embodiments, a wearable device attached to the youth can communicate with the mobile application running on the parent's mobile device and/or a mobile application running on the child's mobile device. Health-related data such as number of steps walked, number of steps climbed, hydration level, and heart rate, for example, can be communicated to either or both mobile applications accordingly.

In some embodiments, the disclosed system can integrate with electronic payment systems managed by third parties for rewarding youths on successfully completing the task. For example, if a parent desires to reward a youth for completing a task successfully, the parent can automatically transfer funds to one or more electronic wallet applications owned/operated by the youth or to a traditional checking or savings account. In some embodiments, a parent rewards a youth by allowing the youth to watch television or play a video game for a certain duration of time. For example, the mobile application in the computing device of the parent can send an electronic signal to an application running on a television in the parent's house, causing the television to turn on for the time period specified in the reward. In some embodiments, if the child misses a task deadline, the child can receive less of a reward than the child would had the child completed the task on time. In some embodiments, the child can be penalized for missing a deadline (e.g., earlier bedtime, reduced television time).

Thus, embodiments of the present disclosure can communicate with a variety of electronic devices, and can receive/transmit data, settings, configuration options, parameters, and the like to these devices. Such data communication can be real time, non-real time, or near real time. In some embodiments, the electronic devices can notify the assigning mobile application program a percentage of completion of the task. That notification can include an image, video, text messages, email message, or any other digital communication indicating a progress of completion of the task. In some embodiments, a wearable device attached to a youth can be used to track the progress of completion of the task.

As used herein, the term "user" is synonymous with the person being assigned tasks such as a youth or a child. That person can be, for example, a child, a pre-teenager, a teenager, or someone who is college age. The term "individual" is used to refer to the task assignor, such as a parent or a legal guardian, and can include relatives and well-wishers, as well. While parents are described in this disclosure as the as the assignor of the tasks and children as the assignee of the tasks, this disclosure contemplates other relationships, as well. For example, using systems and methods described herein, an employer can assign tasks to employees and track the employee's progress using one or more devices. In another example, a health insurance company can assign tasks (e.g., walk three miles) to the insured for a reward of a lower insurance bill. As mentioned, any relationship in which one party is assigning a task to a second party is contemplated by this disclosure. Other examples include teaches assigning tasks to students, one sibling assigning a task to another sibling, and an insurance company assigning "safe driving" tasks to an insured customer.

In the following description, for the purposes of explanation, numerous specific details are set forth in order to provide a thorough understanding of embodiments of the present disclosure. However, it will be apparent on reading the disclosure to one skilled in the art that embodiments may be practiced without some of these specific details.

Moreover, the techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions that may be used to program a computer (or other electronic devices) to perform a process. The machine-readable medium may include, but is not limited to, floppy diskettes, optical disks, compact disc read-only memories (CD-ROMs), magneto-optical disks, read-only memories (ROMs), random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

FIG. 1 illustrates an example of a network-based operating environment 100 in which some embodiments of the present disclosure may be used. As illustrated in FIG. 1, operating environment 100 may include applications 105A-105N running on one or more computing devices 110A-110M (such as a mobile device; a mobile phone; a telephone; a tablet computer; a mobile media device; a mobile gaming device; a vehicle-based computer; a dedicated terminal; a public terminal, desktop, or laptop computer; a kiosk; wearable devices such as a smartwatch; etc.). In some embodiments, applications 105A-105N may be stored on one or more computing devices 110A-110M or may be stored remotely on a server (in the "cloud"). These computing devices can include mechanisms for receiving and sending traffic by connecting through network 115 to task manager platform 120, sensors 135A-135N, and data stores 125 and 130.

FIG. 1 also shows sensor 135A-135N connected via network 115 to task manager platform 120. These sensors can be integrated within or coupled to electronic devices, vehicles, and other objects and can monitor and/or collect data. For example, a sensor 1 can be coupled to a water heater, a sensor 2 can be coupled to a refrigerator, a sensor 3 can be coupled to a dishwasher system, a sensor 4 can be coupled to a washer, a sensor 5 can be coupled to a user's car, a sensor 6 can be coupled to the user. These sensors can periodically or intermittently monitor the devices and transmit operating data of the devices, or health data of the user, to the task manager platform 120.

In some embodiments, more than one sensor may be coupled to a device or a vehicle. For instance, a first sensor can be coupled to the transmission system of a user's car, and a second sensor can be coupled to the distributor of the car. The sensors can be running one or more application software or operating system software, and can include one or more processors. In some embodiments, the sensors can exchange data and information among themselves. In some embodiments, sensors can communicate with one or more applications 105A-105N running on the computing devices 110A-110M. Thus, for example, a sensor can communicate data to a mobile application program running on a parent's mobile device and/or a youth's mobile device. For purposes of discussion and explanation herein, the term "sensor" is considered to be synonymous with the electronic device to which they are coupled, and hence are used interchangeably.

Computing devices 110A-110M may be configured to communicate via the network 115 with task manager platform 120. In some embodiments, computing devices 110A-110M can retrieve or submit information to task manager platform 120 and run one or more applications with customized content retrieved by task manager platform 120 and data stores 125 and 130. For example, computing devices 110A-110M can execute a browser application or a customized client to enable interaction between the computing devices 110A-110M, task manager platform 120, and data stores 125 and 130. In some embodiments, task manager platform 120 can be a server remotely located from the electronic devices. In some embodiments, the task manager platform 120 can be in close proximity with the electronic devices. Furthermore, the task manager platform 120 can be located at the parent's residence. In alternative embodiments, the task manager platform 120 can be located at a facility external to the parent's residence. In some embodiments, the task manager platform 120 works in a distributed manner, and thus some components can be at a parent's residence, and some other components can be located outside the parent's residence. Task manager platform 120 can be running on one or more servers and can be used to receive operating data from the sensors, create tasks for users, manage the completion of the tasks, store user profiles and/or financial data in data stores 125 and 130, and/or perform other activities.

Network 115 can be any combination of local area and/or wide area networks, using wired and/or wireless communication systems. Network 115 can be, or could use, any or more protocols/technologies: Ethernet, IEEE 802.11 or Wi-Fi, worldwide interoperability for microwave access (WiMAX), cellular telecommunication (e.g., 3G, 4G, 5G), CDMA, cable, digital subscriber line (DSL), etc. Similarly, the networking protocols used on network 115 may include multiprotocol label switching (MPLS), transmission control protocol/Internet protocol (TCP/IP), User Datagram Protocol (UDP), hypertext transfer protocol (HTTP), simple mail transfer protocol (SMTP), and file transfer protocol (FTP). Data exchanged over network 115 may be represented using technologies, languages, and/or formats, including hypertext markup language (HTML) or extensible markup language (XML). In addition, all or some links can be encrypted using conventional encryption technologies such as secure sockets layer (SSL), transport layer security (TLS), and Internet Protocol security (IPsec).

Data stores 125 and 130 can be used to manage storage and access to user data such as user profiles, operating data of sensors, user's financial and personal data, data received from third parties, one or more tasks delegated by a parent to a youth, settings and parameters associated with the task, educational materials such as videos or electronic manuals that can be used in completing the task, and other information. Data stores 125 and 130 may be a data repository of a set of integrated objects that are modeled using classes defined in database schemas. Data stores 125 and 130 may further include flat files that can store data. Task manager platform 120 and/or other servers may collect and/or access data from the data stores 125 and 130. Information provided by users can be stored in data stores 125 and 130.

Figure 2:
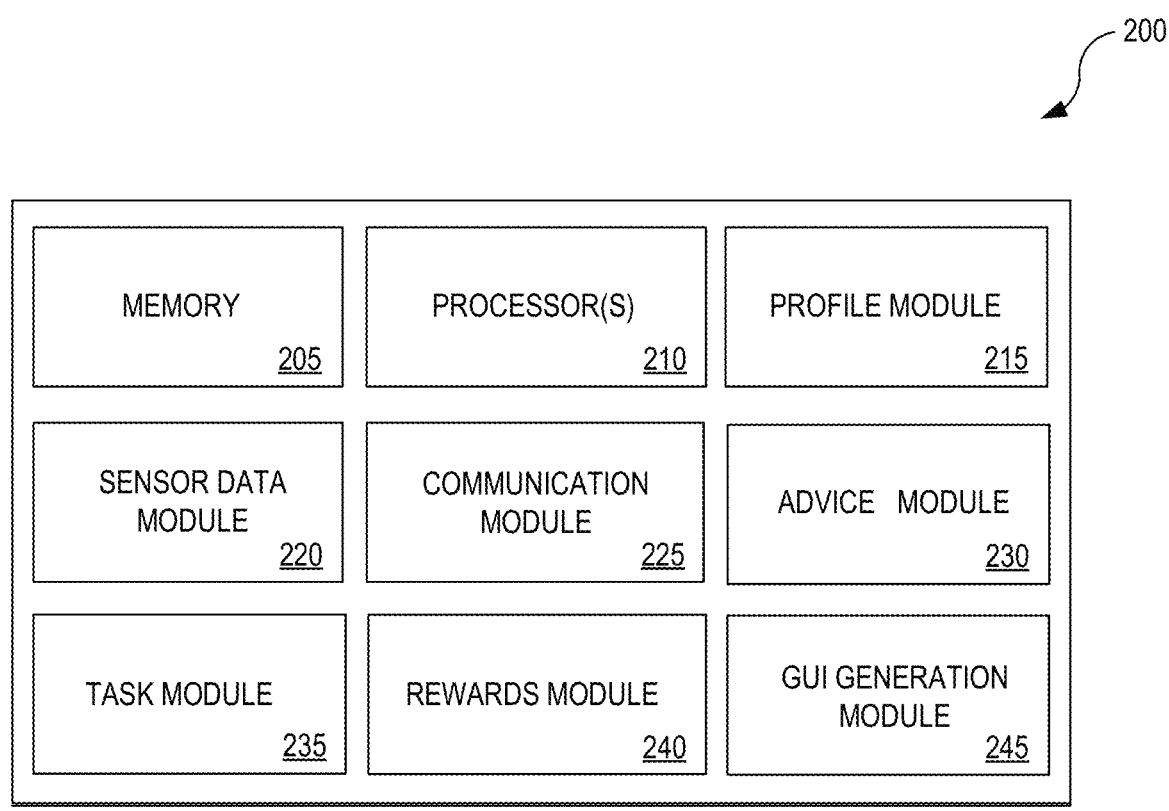
FIG. 2 illustrates various components of a task manager platform that may be used in accordance with various embodiments of the present disclosure.

FIG. 2 illustrates a set of components 200 within a system such as task manager platform 120 according to one or more embodiments of the present disclosure. In some embodiments, these components can be included inside one or more computing devices 110A-110M of a user (e.g., youth) or a parent. According to the embodiments shown in FIG. 2, task manager platform 120 can include memory 205, one or more processors 210, profile module 215, sensor data module 220, communication module 225, advice module 230, task module 235, rewards module 240, and GUI generation module 245. Other embodiments of the present invention may include some, all, or none of these modules and components, along with other modules, applications, and/or components. Still yet, some embodiments may incorporate two or more of these modules and components into a single module and/or associate a portion of the functionality of one or more of these modules with a different module. The components included in a youth's computing device can either be the same or different than those included in a parent's computing device.

Memory 205 can store instructions for running one or more applications or modules on processor(s) 210. For example, memory 205 could be used in one or more embodiments to house all or some of the instructions needed to execute the functionality of profile module 215, sensor data module 220, communication module 225, task module 235, and GUI generation module 245. Generally, memory 205 can include any device, mechanism, or populated data structure used for storing information. In accordance with some embodiments of the present disclosure, memory 205 can encompass, but is not limited to, any type of volatile memory, nonvolatile memory (RAM), and dynamic memory. For example, memory 205 can be random access memory, memory storage devices, optical memory devices, magnetic media, floppy disks, magnetic tapes, hard drives, SIMMs, SDRAM, DIMMs, RDRAM, DDR RAM, SODIMMS, EPROMs, EEPROMs, compact discs, DVDs, and/or the like. In accordance with some embodiments, memory 205 may include one or more disk drives, flash drives, one or more databases, one or more tables, one or more files, local cache memories, processor cache memories, relational databases, flat databases, and/or the like. In addition, those of ordinary skill in the art will appreciate many additional devices and techniques for storing information that can be used as memory 205.

Profile module 215 can create personal and financial profiles for users and parents. Personal data of a user or a parent can include a name, an address, a phone number, an email, and a photograph of the user and/or associated parent. Profiles may include users' and parents' personal data; bank/financial institution data; credit card/debit card data, including electronic wallet identification information; and a list of objects (e.g., devices, dishwashers, refrigerators, vehicles, mobile devices, light bulbs) associated with or owned by the user, and information regarding the objects associated with the user (e.g., make, model, date purchased). For example, in some embodiments, profile data for a parent can include the list of devices that a parent owns and related specifications of the devices. In some embodiments, profiles can include a list of vehicles and configuration/operational settings of the vehicles that a user/parent operates. The profile module 215 can query a networked database to retrieve profile information of users and parents. Such profile information can be stored in the "cloud," or it can be physically coupled to profile module 215.

Sensor data module 220 can determine operational characteristics, settings, and/or configuration data of one or more sensors that are associated with a user's objects and can also include information that identifies various events with a sensor (e.g., the end of usable life of a device or a vehicle). Sensor data module 220 can, for example, determine that the dishwasher needs to be unloaded, and task module 235 may create a task for unloading the dishwasher. In a further example, sensor data module 220 can identify that the brake pads in a user's vehicle will need to be replaced within an estimated timeframe. Sensor data module 220 can determine that the engine oil in a parent's automobile needs to be changed. According to aspects disclosed herein, a sensor can be "any" (i.e., without any limitation) kind of sensor, from any manufacturer, for a variety of data monitoring purposes, and can collect different forms of operating data. For example, a sensor can be coupled to (or included as a component inside) various types of equipment, such as medical diagnostic equipment at a user's home or a doctor's clinic, or even wearable devices attached to a user's body. Thus, such sensors can monitor and collect health data of a user.

In some embodiments, sensor data module 220 can receive telematics data for automobiles driven by a user or a parent. In such embodiments, the electronic device is the automobile the youth operates, and a sensor device in the automobile is configured for transmitting telematics data (e.g., in real time, near real time, or non-real time at periodic or intermittent intervals) of the automobile to a remote mobile application program (e.g., running on a parent's computing device) via Global Positioning System (GPS) technology.

Sensor data module 220 can also store network communication data such as an IP address for communicating with the operating sensors. In some scenarios, the sensors installed in a user's home or business communicates via a gateway or a router. In such scenarios, the IP address of the gateway or the router would be stored in the sensor data module 220.

Communication module 225 facilitates communication with electronic devices (e.g., sensors) and mobile application programs via wireless communication methods such as a near field communication (NFC), Bluetooth, and Wi-Fi. For example, communication module 225 can receive operating data from electronic devices in connection with a task of a user. The operating data can, for example, include location data of the user. The user's location may be sent by the electronic device in response to the electronic device detecting that the user is in close proximity to the electronic device. For example, location data may indicate that a user (youth) is close to the dishwasher or close to the dryer.

In some embodiments, communication module 225 can have geolocation (e.g., GPS) capabilities. In such embodiments, a user's computing device can determine a location of the user based on the geolocation capability. This location information can be conveyed to task manager platform 120. The task manager platform 120 can create tasks assigned to the user based on the user's location.

In some embodiments, communication module 225 can receive information relating to tasks that depend on health choices of the user. When the user is performing the task, the mobile application program running on the parent's computing device can receive health data, for example, from one or more wearable computing devices attached to the user. The wearable computing device can be a consumer-wearable device such as a band or necklace attached to a user's body. In some instances, the consumer-wearable device can be a user's mobile phone. The consumer-wearable device can send health data or fitness/physical exercise data (e.g., number of steps walked or number of miles ran) directly to the second mobile application program. The health data can include a number of steps walked, a number of calories burned, a number of miles ran, a number of miles biked, a number of miles swam, an amount of weight lifted during a workout, a number of repetitions and sets of an exercise performed, a time duration of the exercise, heartrate, body weight, body density, pulse, or a type of exercise. Thus, when the user is performing the task, communication module 225 on the parent's computing device or the youth's computing device, or on both devices, can continuously receive the health data.

Advice module 230 facilitates delivery of advice to a user regarding steps taken to complete a task. For example, a parent can provide instructions with the help of images, text, or videos in connection with completing the task. For example, if a parent has tasked a youth with changing the oil in the car, the parent can send a demonstration video that teaches how to the change the oil. Advice module 230 may further provide advice to the parent in assigning certain tasks (e.g., based on the child's age or past performance) and providing rewards (e.g., $4.00 for mowing the grass). In some embodiments, such information can be crowdsourced and provided to the parent.

Task module 235 facilitates task creation for users. Examples of tasks can include mowing the grass, doing homework, unloading the dishwasher, picking up a sibling from school, or running a mile. The settings of the task, for example, can be a deadline (i.e., date and/or time of day) before which the dishwasher needs to be run, before which the lawn needs to be mowed, before which a washing machine or a dryer needs to be run, or any other parameters or settings associated with the task. In some embodiments, if the task is not completed by the deadline, the rewards can be lowered or removed. In some embodiments, the child can be penalized for not completing a task on time (e.g., funds can be removed from the child's account, the child's video game or television time can be reduced). In some embodiments, the settings for the task can include audio/video (NV) content specifying steps of the task, or images and textual content specifying steps of the task. In some embodiments, task module 235 can create a mapping of related or linked tasks.

In some embodiments, task module 235 on the parent's computing device can send or receive task-related notifications from electronic devices, including tasks that are "open" (e.g., tasks that are approaching their due dates and have not been completed by a user). A task module 235 running on a parent's computing device can also communicate with a task module 235 running on a youth's computing device, and vice versa. In some embodiments, a task might need to be updated while it is being completed by the youth. In such embodiments, task updates can be sent and/or received by the computing devices of the parent and/or the youth. When a user has completed a task, that task is removed.

In some embodiments, task module 235 keeps a log of all past tasks delegated to a user, or successfully performed by a user. In some embodiments, the child sends an indication to the parent application that the task is complete. Then, the parent can "Approve" the task. Once the completed task is approved, the parent's application can send an approval to the child's application that the task has been completed to the parent's satisfaction and the child can be rewarded. In some embodiments, the electronic device can notify the parent's mobile application that the has been completed. The approval can be in response to the parent reviewing an image, video, or audio (e.g., sent by the electronic device) in connection with completion of the task. The image can, for example, reflect if the dishes in the dishwasher are clean, or show that the clothes in the dryer are dry. In some situations, a task can be rejected by a parent.

In some embodiments, task module 235 can allow sharing of task-related information among a group of youths so as to foster healthy competition (e.g., among siblings). In some embodiments, a competitive youth can request a parent to create more tasks. In such embodiments, task module 235 running on a youth's computing device can propose tasks to a parent. In some embodiments, task module 235 running on a parent's computing device can delegate a collection of tasks to a youth, and the associated priority of completing those tasks. In some embodiments, a parent or a youth or both can set goals in terms of completing certain tasks or earning financial rewards in connection with those tasks.

Rewards module 240 facilitates creation and delivery of a rewards program upon successful completion of a task by a user. The rewards can be monetary or they can be customized for a specific scenario (e.g., a youth is rewarded with a pizza for dinner). In some embodiments, a parent can reward a youth by allowing the youth to watch television for a certain duration of time. Thus, for example, the mobile application in the computing device of the parent can send an electronic signal to a mobile application running on a television in the parent's house causing the television to turn on for a time period. A parent can review the rewards redeemed by a user, uses of the rewards, balances in the youth's financial account, pending cash transfers, etc. The rewards can also be paid electronically (e.g., electronic payment is transmitted to a youth's electronic wallet application for transfer of funds to a financial account of the youth). In some embodiments, rewards module 240 can set a target limit on the amount of rewards that can be earned by a youth over a duration of time (e.g., daily, weekly, monthly). In some embodiments, a parent can motivate a youth to donate to charity. In such embodiments, a youth can have the option to donate to charity or spend the monetary reward amount earned. In some scenarios, a parent can match a youth's charitable donations so as to motivate the youth to develop better social values and awareness.

GUI generation module 245 can generate one or more GUI screens that allow for interaction with a user. In at least one embodiment, GUI generation module 245 generates a graphical user interface receiving and/or conveying information (e.g., a list of tasks provided by task module 235) to the user's computing device. The GUI generation module 245 on a youth's computing device may be similar or different than a GUI generation module 245 on a parent's computing device. In some embodiments, GUI generation module 245 can display avatars and other choices for user interface (UI) display that can be selected by a youth or by a parent to represent their character.

Figure 3:
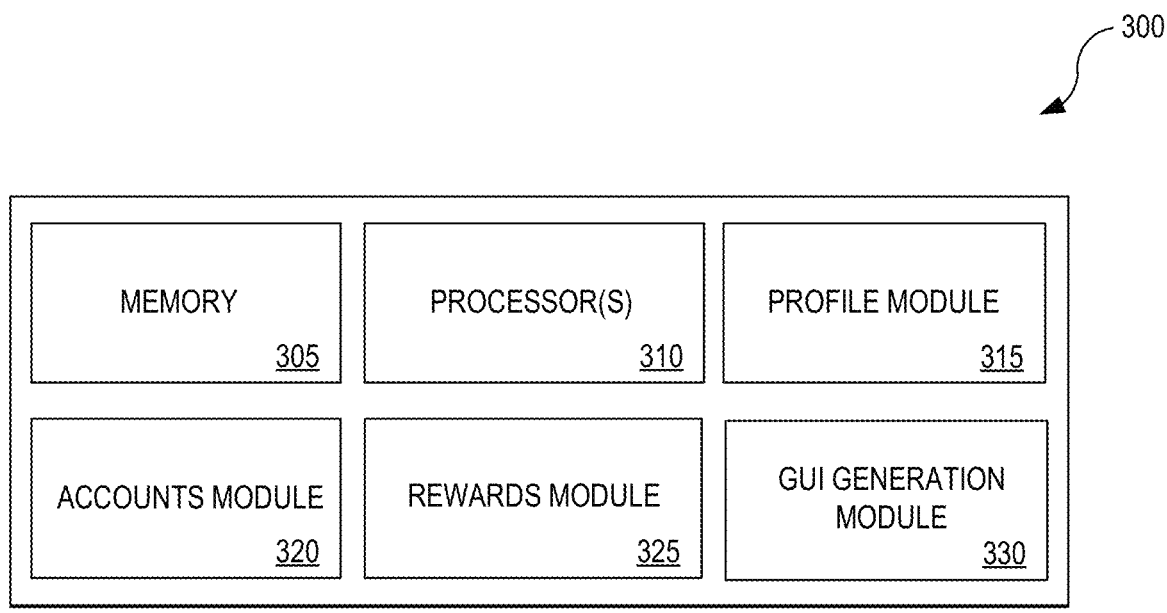
FIG. 3 illustrates various components of a task manager platform that may be used in accordance with various embodiments of the present disclosure.

FIG. 3 illustrates a set of components 300 within a system such as task manager platform 120 according to one or more embodiments of the present disclosure. In some embodiments, these components can be included in a server maintained by the entity that owns and operates task manager platform 120. According to the embodiments shown in FIG. 2, task manager platform 120 can include memory 305, one or more processors 310, profile module 315, accounts module 320, rewards module 325, and GUI generation module 330. Other embodiments of the present invention may include some, all, or none of these modules and components along with other modules, applications, and/or components. Still yet, some embodiments may incorporate two or more of these modules and components into a single module and/or associate a portion of the functionality of one or more of these modules with a different module. The components included in a youth's computing device can either be the same or different than those included in a parent's computing device.

Memory 305 can be any device, mechanism, or populated data structure used for storing information, as described above for memory 205. Memory 305 can store instructions for running one or more applications or modules on processor(s) 310. For example, memory 305 could be used in one or more embodiments to house all or some of the instructions needed to execute the functionality of profile module 315, accounts module 320, rewards module 325, and GUI generation module 330.

Profile module 315 can maintain profiles for users and parents that reflect the personal and financial profiles of the users and the parents, similar to the profiles described with respect to profile module 215.

Accounts module 320 facilitates transfer of financial rewards from a parent account to a financial account of a youth. Thus, for example, a parent can reward a youth for completed tasks by transferring money into the youth's account. In some embodiments, accounts module 320 can interact with banks and financial institutions for transfer of the money. In some embodiments, the disclosed system can integrate with electronic payment systems managed by third parties for rewarding youths on successfully completing the task. For example, if a parent desires to reward a youth for completing a task successfully, the funds can be automatically transferred from the parent's electronic wallet or account to the child's electronic wallet or account.

Rewards module 325 facilitates the offer and redemption of monetary and non-monetary rewards upon successful completion of tasks. Functionality of the rewards module 325 can be similar to the functionality of the rewards module 240 included in a computing device of a user and/or a parent.

Figure 4:
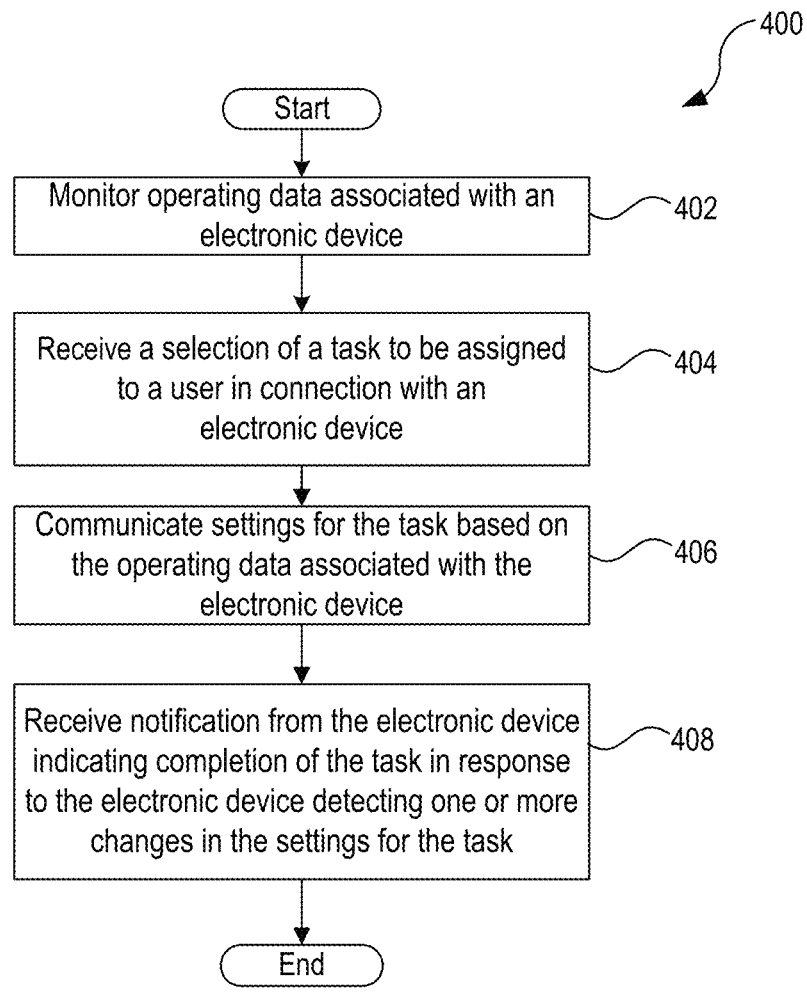
FIG. 4 is a flowchart illustrating a set of operations for automated task management in accordance with various embodiments of the present disclosure.
Figure 5:
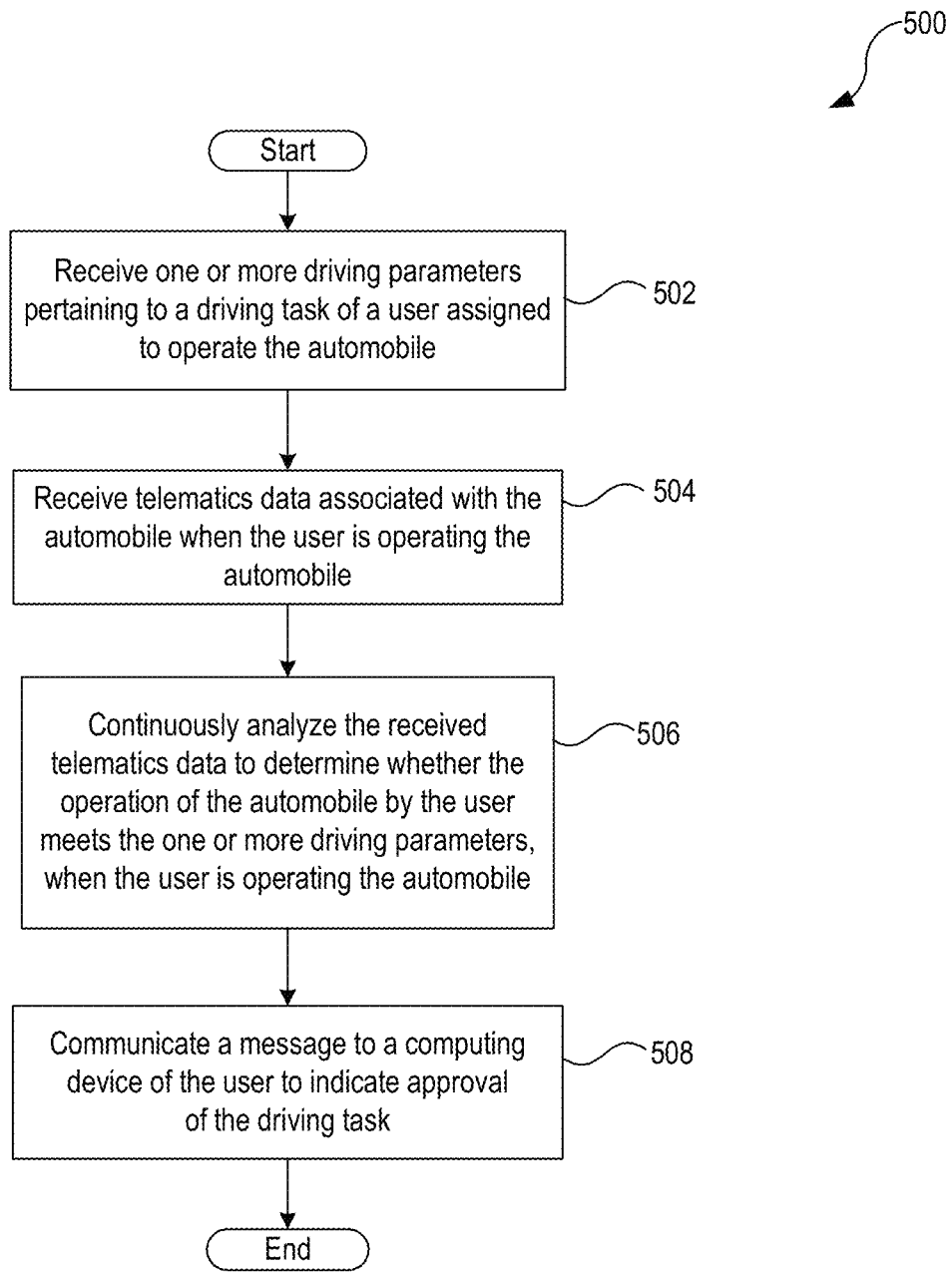
FIG. 5 is a flowchart illustrating a set of operations for automated task management in accordance with various embodiments of the present disclosure.
Figure 6:
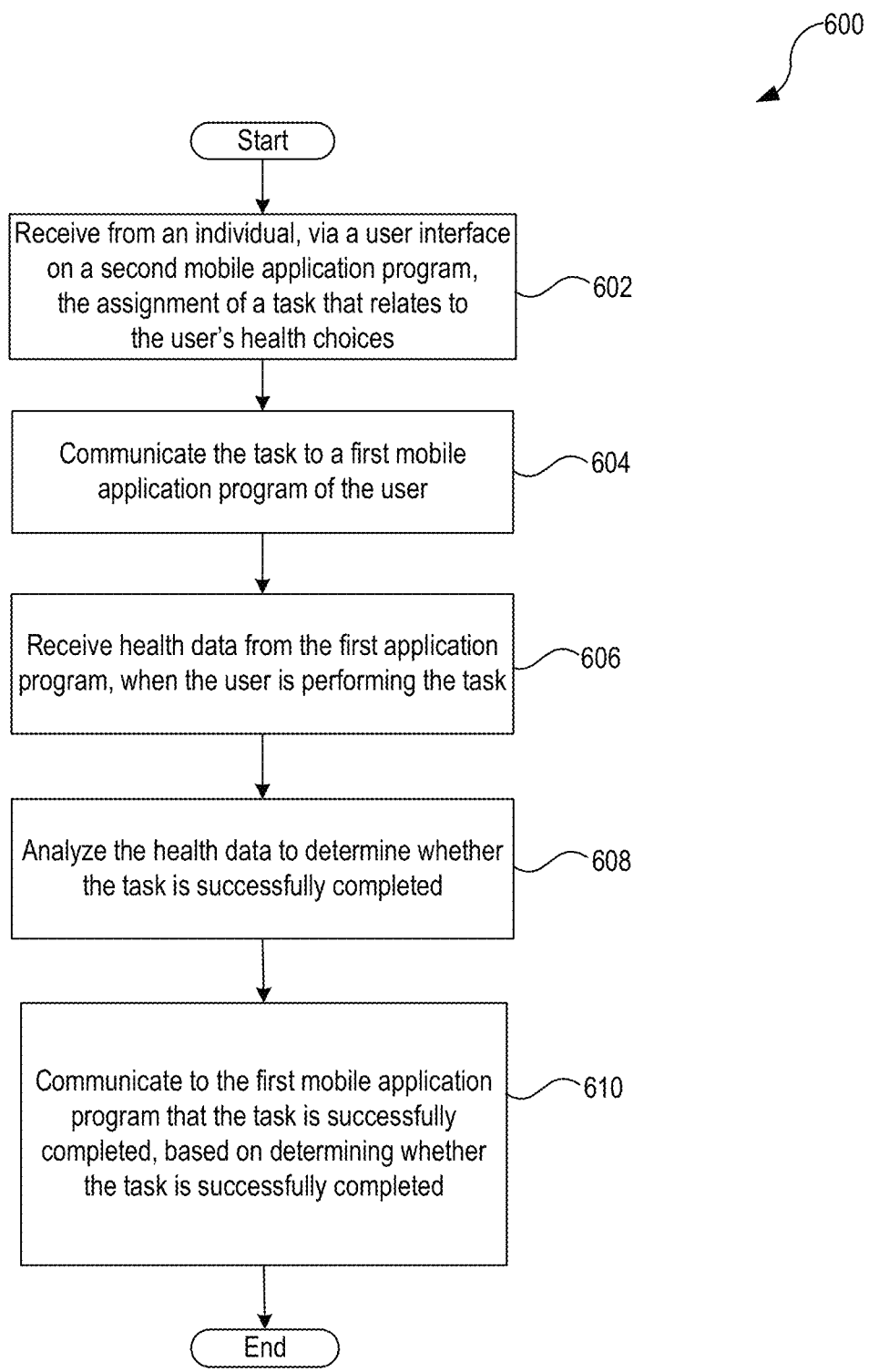
FIG. 6 is a flowchart illustrating a set of operations for automated task management in accordance with various embodiments of the present disclosure.

GUI generation module 330 can generate one or more GUI screens that allow for interaction with a user. In at least one embodiment, GUI generation module 330 generates a graphical user interface receiving and/or conveying information to the user's computing device and/or the parent's computing device. The GUI generation module 330 on a youth's computing device may be similar or different than a GUI generation module 330 on a parent's computing device. In some embodiments, GUI generation module 330 can display avatars and other choices for user interface (UI) display that can be selected by a youth or by a parent to represent their character. FIGS. 4-6 are flowcharts illustrating sets of operations for automated task management. In some embodiments, fewer than all of the operations in each set of operations are performed, whereas in other embodiments additional operations are performed. Moreover, in some embodiments, the operations may be performed in different orders or in parallel. The operations can be performed by various components of task manager platform 120 such as those illustrated in FIG. 2 and/or FIG. 3.

FIG. 4 is a flowchart illustrating a set of operations 400 for automated task management in accordance with various embodiments of the disclosure. In some embodiments, the set of operations 400 can be performed by a mobile application running on a computing device of a parent or a legal guardian (e.g., also referred to as an "individual" herein) or a youth (e.g., also referred to as a "user" herein). Monitor operation 402 monitors operating data associated with an electronic device (e.g., a dishwasher, an oven, an automobile) in a collection of electronic devices (e.g., at the parent's home). The operating data can, for example, include location data of the user, wherein the location data of the user is sent by the electronic device in response to the electronic device detecting that the user is in close proximity to the electronic device (e.g., that a user (youth) is close to the dishwasher or close to the dryer).

Receive operation 404 receives a selection of a task (e.g., via a user interface of the mobile app) to be assigned to a user. The task can be any task, such as, but not limited to, unloading a dishwasher, loading the dishwasher, rotating tires of an automobile, changing the engine oil of an automobile, cleaning an oven, cleaning a grill, cleaning a refrigerator, going to a location in the automobile, taking the trash out, and putting air in the tires of a car. Communicate operation 406 communicates settings of the task to an electronic device. The settings of the task, for example, can be a deadline (e.g., date and/or time of day) before which the dishwasher needs to be run, before which the lawn needs to be mowed, before which a washing machine or a dryer needs to be run, or any other parameters or settings associated with the task. In some embodiments, the settings for the task can include audio/video (NV) content specifying steps of the task, or images and textual content specifying steps of the task.

Receive operation 408 receives a notification from the electronic device indicating completion of the task, in response to the electronic device detecting one or more changes in the settings of the task. The one or more changes in the settings of the task can, for example, include an end of a wash cycle, an end of a dry cycle, an end of a dishwashing cycle, a change in the weight/volume of the dishwasher indicating the end of a dishwashing cycle, a tire pressure monitor included in an automobile indicating the tires are full, a change-engine oil sensor indicating that the engine oil in an automobile has been replaced. The process terminates thereafter.

In some embodiments, the child's mobile application receives an approval from the parent reflecting that the task has been completed to the parent's satisfaction. Such approval can, for example, come after the electronic device notifies the mobile application of the parent that the task is completed. The approval can be in response to the parent reviewing an image, video, or audio (e.g., sent by the electronic device) in connection with completion of the task. The image can, for example, reflect if the dishes in the dishwasher are clean, or show that the clothes in the dryer are dry. In some embodiments, the operating data associated with the electronic device is in a first type of electronic format (e.g., a particular type of file format), and the notification from the electronic device indicating completion of the task is in a second type of electronic format (e.g., in a different type of file format). In some embodiments, upon receiving the notification from the electronic device indicating completion of the task, the mobile application in the computing device of the parent sends an electronic signal to a mobile application running on a television, for example, the electronic signal causing the television to turn on for a time period. This would provide some kind of reward to the youth for his or her successful completion of the task. The rewards can also be in the form of electronic payments transmitted to a youth's electronic wallet application for transfer of funds to a financial account of the youth.

FIG. 5 is a flowchart illustrating a set of operations 500 for automated task management in accordance with various embodiments of the disclosure. Specifically, the task in FIG. 5 can be a driving-related task of a user assigned to operate an automobile, for example, a youth driving the parent's car to take the younger sister to soccer practice. The steps in FIG. 5 can be performed by a mobile application running on a computing device of a parent. In such embodiments, the electronic device is the automobile the youth operates and a sensor device in the automobile is configured for transmitting telematics data (e.g., in real time, near real time, or non-real time, at periodic or intermittent intervals) of the automobile to a remote mobile application program (e.g., running on a parent's computing device) via Global Positioning System (GPS) technology.

Receive operation 502 receives one or more driving parameters pertaining to a driving task (e.g., running an errand by driving the parent's car to the drycleaners or grocery store) of a user assigned to operate the automobile. Thus, via a user interface on the mobile application program of the parent's computing device, the parent can set various driving parameters to which the parent would like the youth to adhere. Examples of parameters can be driving below a certain speed limit, driving along a particular route, driving with the sound in the car stereo below a certain threshold volume level, driving with headlights on, driving without jackrabbit starts and stops, driving with seatbelts on, driving with a safe bumper distance from the automobile in front and rear, driving without too frequent lane changes, driving with roadside safety precautions, driving with the wipers on when it is raining, following safe parking measures, and other such parameters.

When the user is driving, receive operation 504 receives the telematics data transmitted by the sensor device in the automobile at the mobile application running on the parent's computing device. Upon receiving the telematics data, and while the user is driving the automobile, or anytime the data is received, analyze operation 506 analyzes the telematics data to determine whether operation of the automobile by the user meets the one or more driving parameters set by the parent. Upon determining that the operation of the automobile by the user meets the one or more driving parameters and, upon successful completion of the driving task, the mobile application running on the computing device of the parent can send a message indicating approval of the driving task to a computing device of the user (e.g., to a youth's cell phone indicating that the driving task of the user was approved by the parent) in communicate operation 508. The process terminates thereafter. In some embodiments, the application sends notifications to the user operating the vehicle only when the user is not operating the vehicle (e.g., based on sensor data).

FIG. 6 is a flowchart illustrating a set of operations 600 for automated task management in accordance with various embodiments of the disclosure. Specifically, the task in FIG. 6 can be a task that relates to health choices of the user (e.g., a youth running or swimming or going to the gym). The steps in FIG. 6 can be performed by a mobile application running on a computing device of a parent. For discussion purposes in FIG. 6, a first mobile application program is assumed to be running on a computing device of a user (e.g., a child) and a second mobile application program is assumed to be running on a computing device of an individual (e.g., a parent).

Receive operation 602 receives (e.g., via a user interface) from the individual a task relating to health choices of the user. Such tasks may be issued when the user is in a particular area (e.g., entering a gym, arriving at a park), or when the user could use additional exercise (e.g., when the user has had limited activity for the time of day, the day, week). Communicate operation 604 then communicates the task to the first mobile application program and/or wearable device. When the user is performing the task, the first mobile application program receives health data, for example, from one or more wearable computing devices attached to the user. The wearable computing device can be a consumer-wearable device such as a band or necklace attached to a user's body. In some instances, the consumer-wearable device can be a user's mobile phone. The consumer-wearable device can send health data or fitness/physical exercise data (e.g., number of steps walked or number of miles ran) directly to the second mobile application program. The health data can include a number of steps walked, a number of calories burned, a number of miles ran, a number of miles biked, a number of miles swam, an amount of weight lifted during a workout, a number of repetitions and sets of an exercise performed, a time duration of the exercise, heart-rate, body weight, body density, pulse, or a type of exercise. Thus, when the user is performing the task, receive operation 606 on the second mobile application program can continuously receive the health data. Analyze operation 608 analyzes the health data to determine whether the task is successfully completed. Based on determining whether the task is successfully completed, communicate operation 610 communicates to the first mobile application program of the user that the task is successfully completed. The process terminates thereafter.

Figure 7:
FIGS. 7-10 illustrate example Graphical User Interfaces ("GUIs") showing automated task management developed in accordance with various embodiments of the present disclosure.
Figure 8:
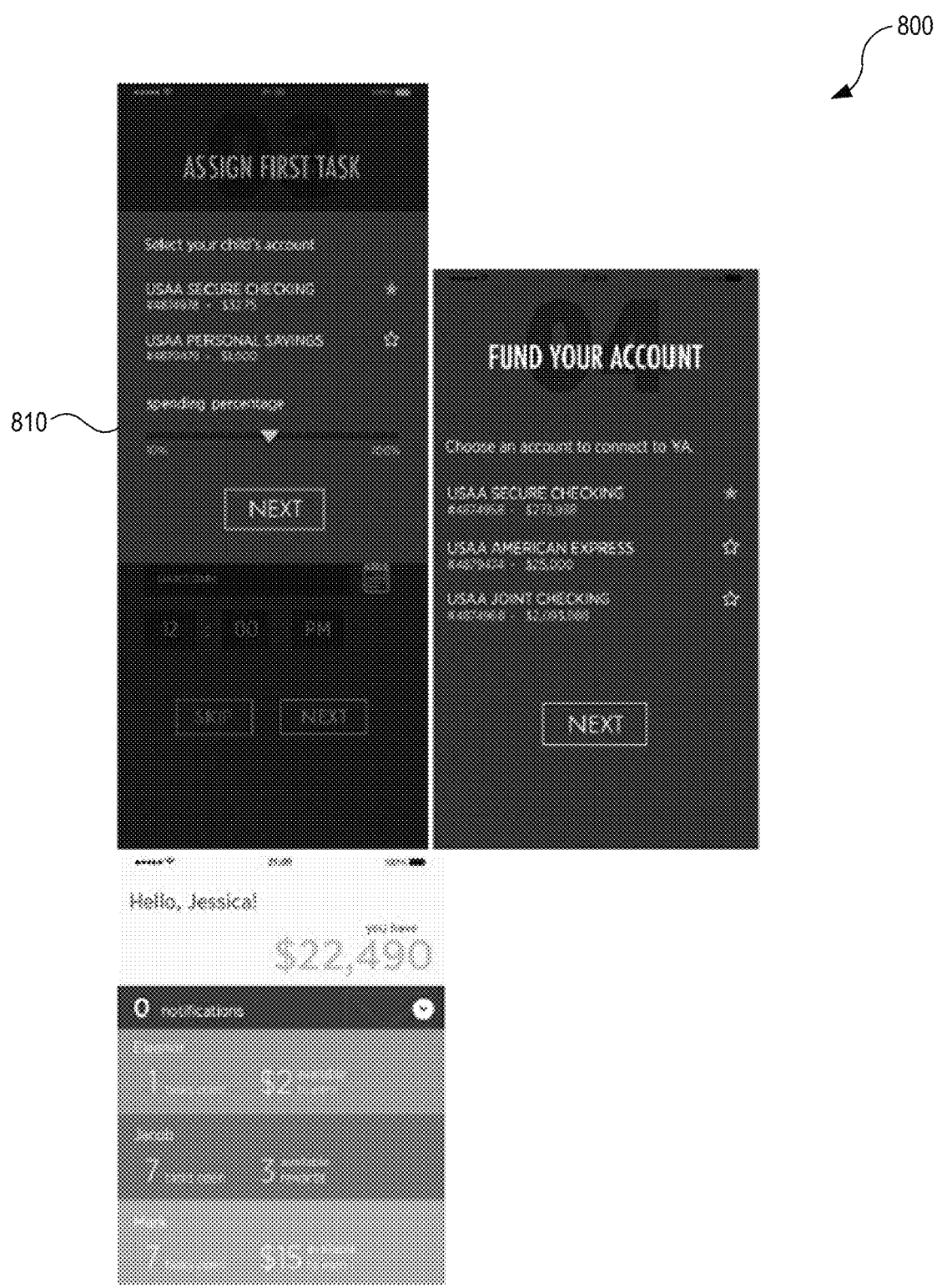
Figure 9:
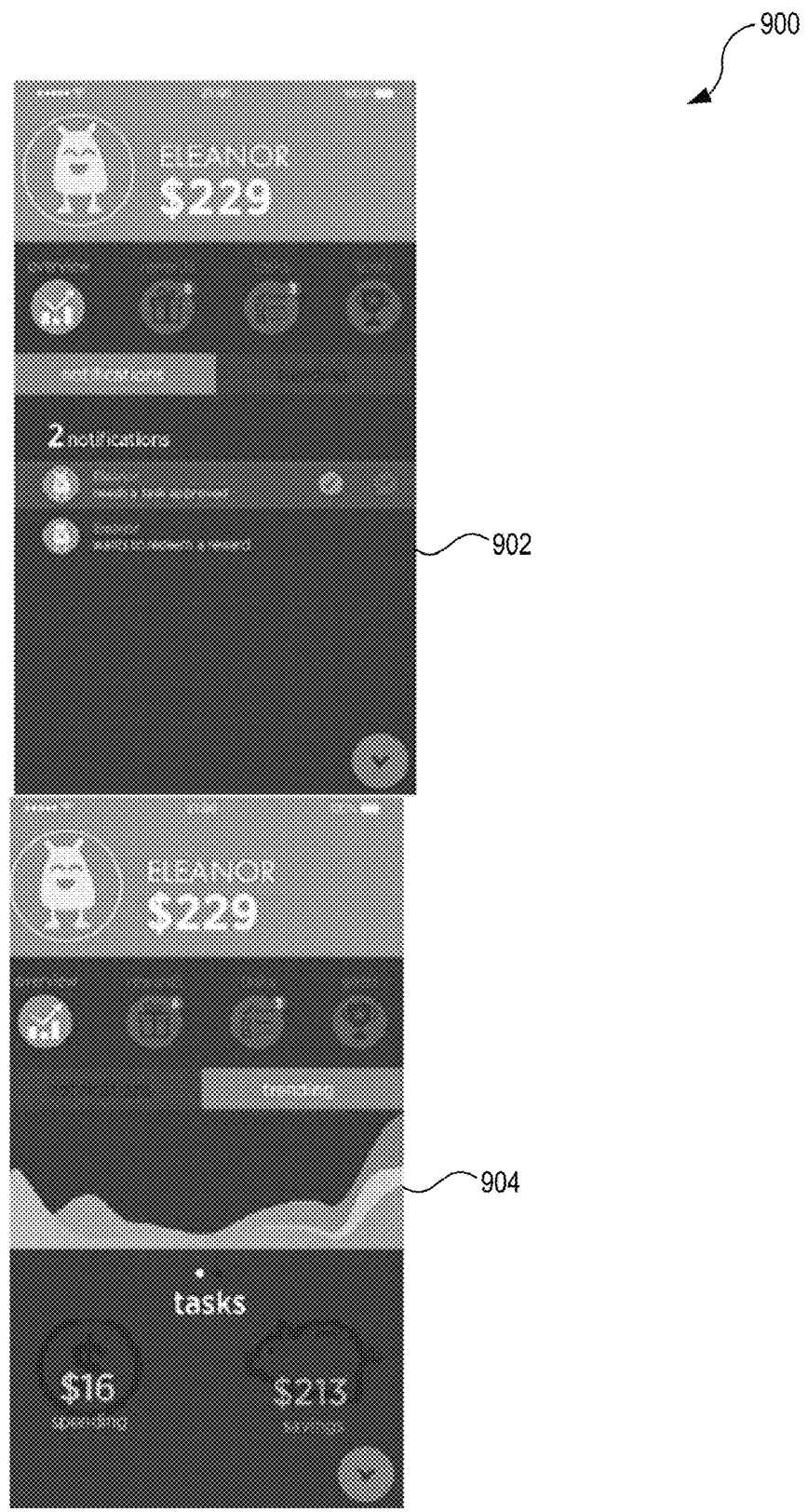

FIGS. 7-9 illustrate example Graphical User Interfaces ("GUIs") showing automated task management developed in accordance with various embodiments of the disclosure. For example, FIG. 7 illustrates various interfaces 700 of a mobile application running on a computing device of the parent. Interface 710 can be used for adding one or more youths (i.e., children named Eleanor, Jacob, and Mark) into the task management mobile application running on the computing device of the parent. Interface 720 can be used to assign tasks to users by the parent. This interface also shows a task, the reward associated with the task, and a due date for the task. Interface 730 can be used to add a youth to the task management system. Interface 740 can be used to assign tasks to the user.

FIG. 8 illustrates interfaces 800 for assigning tasks to users. A parent can, for example, select a financial account of the youth, such as a savings or a checking account, for transferring money upon completion of tasks. Slider bar 810 demonstrates a parent can set a spending percentage on behalf of the youth. Such a percentage is exclusive of the money earned by a youth and is deposited into his or her savings account. In some embodiments, the spending percentage does not include the money that the child is required to put into savings, teaching the child how to save.

Figure 10:
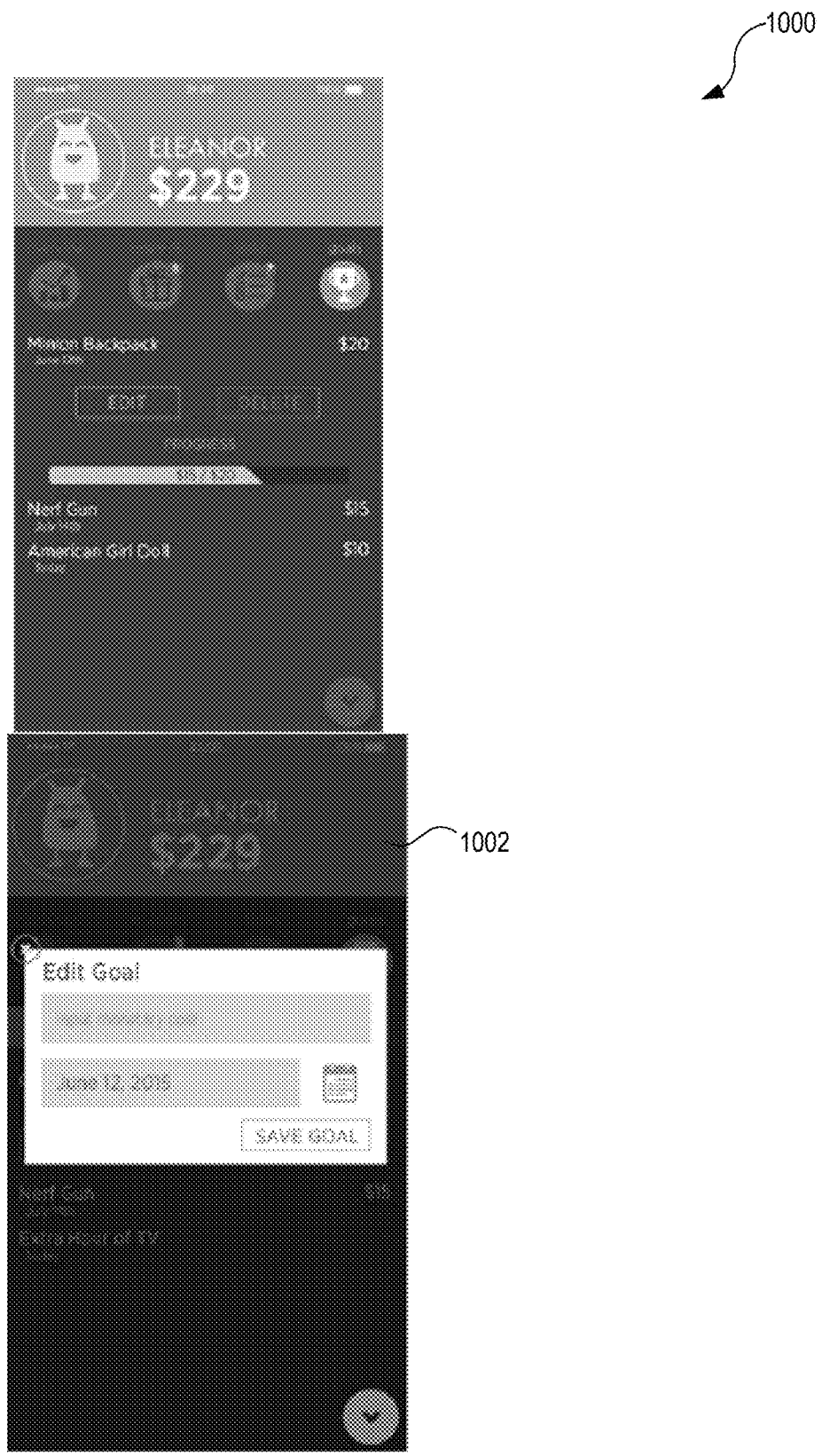

FIGS. 9 and 10 illustrate task management interfaces 900 and 1000. In some embodiments, a youth can be notified when his or her task gets approved. As shown in region 902, a youth Eleanor is waiting for a task to be approved, which allows her to redeem a reward. In some embodiments, task manager platform 120 can receive updates in connection with completion of tasks in real time from electronic devices associated with the task. For example, if a youth is tasked with mowing a lawn, then the lawnmower can send a notification to a parent's mobile application indicating progress of completion of the lawn mowing task, as depicted in region 904 of the interface. FIG. 10 depicts a task management interface 1000 for setting financial goals for a youth. For example, as depicted in region 1002, a youth Eleanor is shown to have earned $229 and given the option to set a financial goal and a date for reaching that goal.

Computer System Overview

Figure 11:
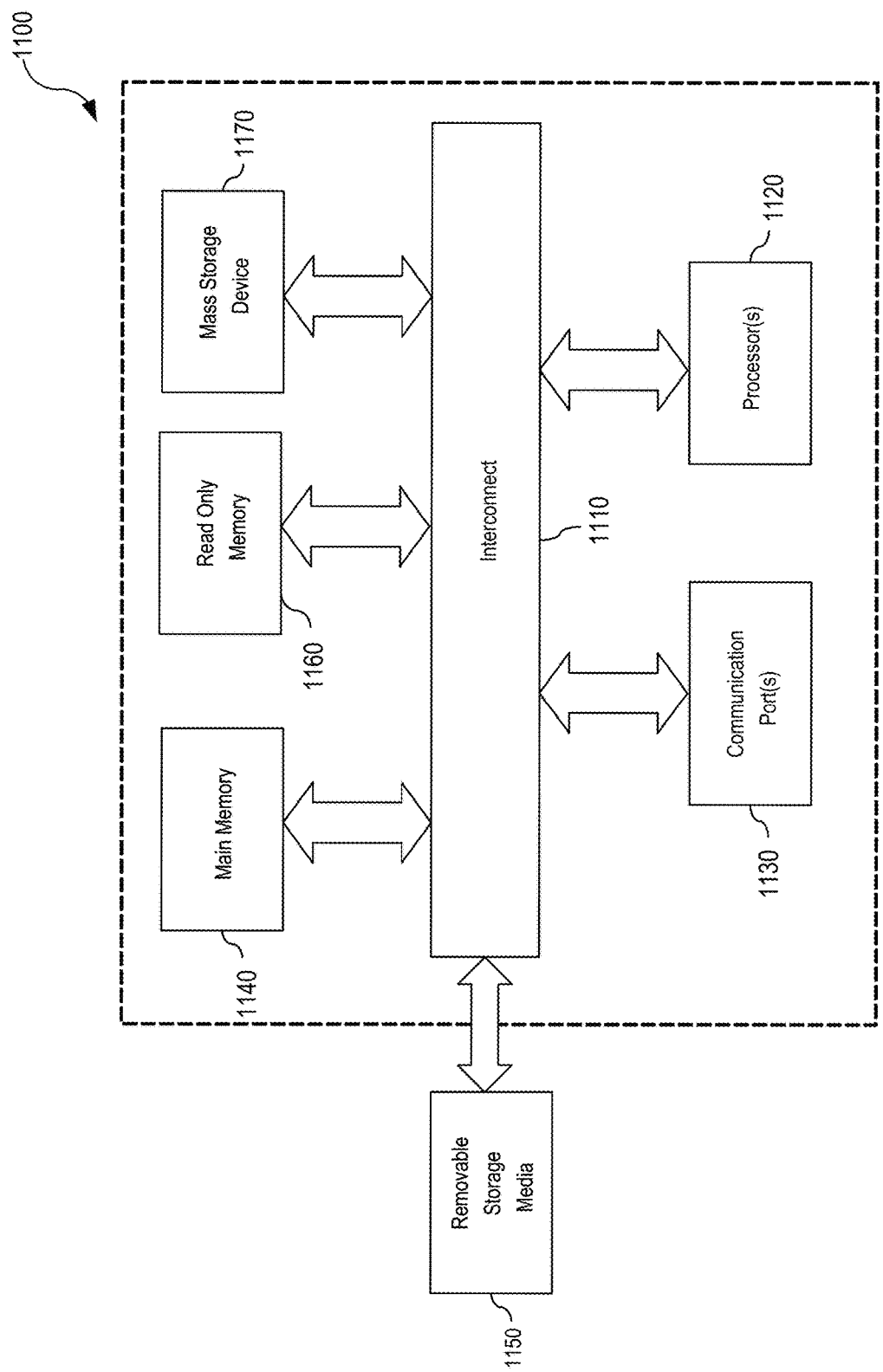
FIG. 11 illustrates an example of a computer system with which some embodiments of the present disclosure may be utilized.

Embodiments of the present disclosure include various steps and operations, which have been described above. A variety of these steps and operations may be performed by hardware components or they may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 11 is an example of a computer system 1100 with which embodiments of the present disclosure may be utilized. According to the present example, the computer system includes an interconnect 1110, at least one processor 1120, at least one communication port 1130, a main memory 1140, a removable storage media 1150, a read only memory 1160, and a mass storage device 1170.

Processor(s) 1120 can be any known processor, such as, but not limited to, an Intel® Itanium® or Itanium 2® processor(s), or AMD® Opteron® or Athlon MP® processor(s), or Motorola® lines of processors. Communication port(s) 1130 can be any of an RS-232 port for use with a modem-based dialup connection, a 10/100 Ethernet port, or a Gigabit port using copper or fiber. Communication port(s) 1130 may be chosen, depending on a network such a Local Area Network (LAN), Wide Area Network (WAN), or any network to which the computer system 1100 connects.

Main memory 1140 can be Random Access Memory (RAM) or any other dynamic storage device(s) commonly known in the art. Read only memory 1160 can be any static storage device(s), such as Programmable Read Only Memory (PROM) chips for storing static information, such as instructions for processor(s) 1120.

Mass storage device 1170 can be used to store information and instructions. For example, hard disks such as the Adaptec® family of SCSI drives, an optical disc, an array of disks such as RAID, the Adaptec family of RAID drives, or any other mass storage devices may be used.

Interconnect 1110 communicatively couples processor(s) 1120 with the other memory, storage, and communication blocks. Interconnect 1110 can be a PCI/PCI-X- or SCSI-based system bus, depending on the storage devices used.

Removable storage media 1150 can be any kind of external hard-drives, floppy drives, USB drives, IOMEGA® Zip Drives, Compact Disc—Read Only Memory (CD-ROM), Compact Disc—Re-Writable (CD-RW), or Digital Video Disc—Read Only Memory (DVD-ROM).

The components described above are meant to exemplify some types of possibilities. In no way should the aforementioned examples limit the disclosure, as they are only exemplary embodiments.

Terminology

Brief definitions of terms, abbreviations, and phrases used throughout this application and the appendices are given below.

The terms "connected" or "coupled" and related terms are used in an operational sense and are not necessarily limited to a direct physical connection or coupling. Thus, for example, two devices may be coupled directly or via one or more intermediary media or devices. As another example, devices may be coupled in such a way that information can be passed therebetween, while not sharing any physical connection with one another. Based on the disclosure provided herein, one of ordinary skill in the art will appreciate a variety of ways in which connection or coupling exists in accordance with the aforementioned definition.

The phrases "in some embodiments," "according to some embodiments," "in the embodiments shown," "in other embodiments," "embodiments," and the like generally mean that the particular feature, structure, or characteristic following the phrase is included in at least one embodiment of the present disclosure and may be included in more than one embodiment of the present disclosure. In addition, such phrases do not necessarily refer to the same embodiments or to different embodiments.

If the specification states a component or feature "may," "can," "could," or "might" be included or have a characteristic, that particular component or feature is not required to be included or have the characteristic.

The term "responsive" includes completely or partially responsive.

The term "module" refers broadly to a software, hardware, or firmware (or any combination thereof) component. Modules are typically functional components that can generate useful data or other output using specified input(s). A module may or may not be self-contained. An application program (also called an "application") may include one or more modules, or a module can include one or more application programs.

The term "network" generally refers to a group of interconnected devices capable of exchanging information. A network may be as few as several personal computers on a Local Area Network (LAN) or as large as the Internet, a worldwide network of computers. As used herein, "network" is intended to encompass any network capable of transmitting information from one entity to another. In some cases, a network may be comprised of multiple networks, even multiple heterogeneous networks, such as one or more border networks, voice networks, broadband networks, financial networks, service provider networks, Internet Service Provider (ISP) networks, and/or Public Switched Telephone Networks (PSTNs) interconnected via gateways operable to facilitate communications between and among the various networks.

Also, for the sake of illustration, various embodiments of the present disclosure have herein been described in the context of computer programs, physical components, and logical interactions within modern computer networks. Importantly, while these embodiments describe various embodiments of the present disclosure in relation to modern computer networks and programs, the method and apparatus described herein are equally applicable to other systems, devices, and networks, as one skilled in the art will appreciate. As such, the illustrated applications of the embodiments of the present disclosure are not meant to be limiting, but instead are examples. Other systems, devices, and networks to which embodiments of the present disclosure are applicable include, but are not limited to, other types of communication and computer devices and systems. More specifically, embodiments are applicable to communication systems, services, and devices such as cell phone networks and compatible devices. In addition, embodiments are applicable to all levels of computing, from the personal computer to large network mainframes and servers.

In conclusion, the present disclosure discloses novel systems, methods, and arrangements for managing tasks, and more particularly, for developing healthy financial habits. While detailed descriptions of one or more embodiments of the disclosure have been given above, various alternatives, modifications, and equivalents will be apparent to those skilled in the art without varying from the spirit of the disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof. Therefore, the above description should not be taken as limiting.

What is claimed is:

1. A non-transitory computer-readable storage medium storing a set of instructions that, when executed by one or more processors, cause a first computing device associated with an individual to perform a process, the process comprising:
   receiving a user-set pre-determined completion time for a task to be assigned to a user;
   monitoring operating data associated with an electronic device, wherein the electronic device is one networked household device in a plurality of networked household devices;
   communicating, via a first electronic notification to the electronic device in the plurality of networked household devices, settings for the task to be assigned to the user based on the operating data associated with the electronic device;
   receiving sensor data associated with the task from the electronic device in the plurality of networked household devices;
   determining a completion of the task by the user based on the sensor data indicating one or more changes in the settings for the task;
   determining the task was completed before the user-set pre-determined completion time for the task based on the sensor data; and
   in response to determining the completion of the task and that the task was completed before the user-set pre-determined completion time, initiating a second electronic notification to a second networked electronic device or an electronic wallet application to initiate a reward.

2. The non-transitory computer-readable storage medium of claim 1, wherein the operating data includes location data of the user, wherein the location data of the user is sent by the electronic device in response to the electronic device detecting that the user is in close proximity to the electronic device.

3. The non-transitory computer-readable storage medium of claim 1, wherein the process further includes:
   receiving, via a user interface, information corresponding to approval of the task in response to receiving the sensor data from the electronic device indicating completion of the task.

4. The non-transitory computer-readable storage medium of claim 1, wherein the process further includes:
   receiving a third electronic notification from the electronic device indicating a percentage of completion of the task.

5. The non-transitory computer-readable storage medium of claim 1, wherein the process further includes:
   receiving a third electronic notification from the electronic device indicating a progress of completion of the task, wherein the third electronic notification includes A) an image, B) a video, C) a text message, D) an email message, or E) other digital communication.

6. The non-transitory computer-readable storage medium of claim 1, wherein the individual can communicate the settings for the task to be assigned to the user to the electronic device via a user interface associated with the first computing device, and wherein the electronic device is selected from at least one of: a dishwasher, an oven, a grill, a refrigerator, a washer, or a dryer.

7. The non-transitory computer-readable storage medium of claim 1, wherein the task is selected from at least one of: unloading a dishwasher, loading the dishwasher, cleaning an oven, cleaning a grill, doing laundry, or cleaning a refrigerator.

8. The non-transitory computer-readable storage medium of claim 1, wherein the operating data associated with the electronic device is in a first type of electronic format and the second electronic notification is in a second type of electronic format.

9. The non-transitory computer-readable storage medium of claim 1, wherein the process includes:
receiving a third electronic notification from a second electronic device in the plurality of networked household devices indicating a second task to be completed, wherein the second task is based on second sensor input from within the second electronic device.

10. The non-transitory computer-readable storage medium of claim 1, wherein in response to receiving the sensor data indicating completion of the task, the process further includes:
initiating a third electronic notification to a second networked device to initiate a reward, wherein the third electronic notification enables turning on the second networked device for a time period.

11. The non-transitory computer-readable storage medium of claim 1, wherein in response to receiving the sensor data indicating completion of the task, the process further includes:
initiating the second electronic notification to the electronic wallet application to cause the electronic wallet application to transfer funds to a financial account associated with the user.

12. The non-transitory computer-readable storage medium of claim 1, wherein in response to receiving the sensor data indicating completion of the task, the process further includes:
initiating a third electronic notification to the electronic wallet application that is configured to manage at least two financial accounts of the user, wherein the third electronic notification to the electronic wallet application causes a transfer of a first fund amount to a first financial account, of the at least two financial accounts of the user, and a second fund amount to a second financial account, of the at least two financial accounts of the user.

13. A method for electronically assigning tasks to a user, the method comprising:
receiving a user-set pre-determined completion time for a task to be assigned to a user;
monitoring operating data associated with an electronic device, wherein the electronic device is one networked device in a plurality of networked devices;
communicating, via a first electronic notification to the electronic device in the plurality of networked devices, settings for a task to be assigned to a user based on the operating data associated with the electronic device;
receiving sensor data associated with the task from the electronic device in the plurality of networked devices;
determining a completion of the task by the user based on the sensor data indicating one or more changes in the settings for the task;
determining the task was completed before the user-set pre-determined completion time for the task based on the sensor data; and
in response to determining the completion of the task and that the task was completed before the user-set pre-determined completion time, initiating a second electronic notification to a second networked electronic device or an electronic wallet application to initiate a reward.

14. The method of claim 13, further comprising receiving a selection of the task to be assigned to the user, the task associated with the electronic device.

15. The method of claim 13, wherein an amount of the reward is a first amount of money, which is transferred to a financial account when the task is performed by a deadline, and the amount of the reward is a second amount of money, which is transferred to the financial account when the task is completed after the deadline, wherein the second amount is less than the first amount.

16. The method of claim 13, further comprising:
receiving at least one of: an image, video content, or audio content associated with the completion of the task; and
receiving information corresponding to approval of the task.

17. A computing system comprising:
one or more processors; and
one or more memories storing instructions that, when executed by the one or more processors, cause the computing system to perform a process comprising:
receiving a user-set pre-determined completion time for a task to be assigned to a user;
monitoring operating data associated with an electronic device, wherein the electronic device is one networked device in a plurality of networked devices;
communicating, via a first electronic notification to the electronic device in the plurality of networked devices, settings for a task to be assigned to a user based on the operating data associated with the electronic device;
receiving sensor data associated with the task from the electronic device in the plurality of networked devices;
determining a completion of the task by the user based on the sensor data indicating one or more changes in the settings for the task;
determining the task was completed before the user-set pre-determined completion time for the task based on the sensor data; and
in response to determining the completion of the task and that the task was completed before the user-set pre-determined completion time, initiating a second electronic notification to a second networked electronic device or an electronic wallet application to initiate a reward.

18. The computing system of claim 17, wherein the process further comprises:
receiving, via a user interface, information corresponding to approval of the task in response to receiving the sensor data from the electronic device indicating completion of the task.

19. The computing system of claim 17, wherein the process further comprises:
in response to receiving the sensor data, initiating a third electronic notification to a second networked electronic device to initiate the reward, wherein an amount of the reward is a first amount of time that the second networked electronic device is allowed to turn on when the task is performed by a deadline and the amount of the reward is a second amount of time that the second networked electronic device is allowed to turn on when the task is completed after the deadline, wherein the second amount of time is less than the first amount of time.

20. The computing system of claim 17, wherein the settings for the task include at least one of: A) audio/video (A/V) content specifying steps of the task or B) images and textual content specifying steps of the task.

* * * * *